United States Patent [19]

Carnes et al.

[11] Patent Number: 4,550,608

[45] Date of Patent: Nov. 5, 1985

[54] OSCILLATING SCANNER AND DRIVE MECHANISM THEREFOR

[75] Inventors: Ronald C. Carnes, Folsom; Ted F. Naumann, Jr., Shingle Springs, both of Calif.

[73] Assignee: General Electric Company, Milwaukee, Wis.

[21] Appl. No.: 566,864

[22] Filed: Dec. 29, 1983

[51] Int. Cl.[4] ............................................. G01N 29/04
[52] U.S. Cl. .................................. 73/633; 128/660; 74/42
[58] Field of Search .......................... 73/633, 618, 620; 128/660; 74/42

[56] References Cited

U.S. PATENT DOCUMENTS 4,215,585  8/1980  Kunii et al. .......................... 73/633
4,282,879  8/1981  Kunii et al. ........................ 128/660
4,418,698 12/1983  Dary ................................... 73/633

OTHER PUBLICATIONS

Chironis, *Mechanisms, Linkages, and Mechanical Controls*, McGraw Hill, 1965, pp. 49–51.

*Primary Examiner*—Anthony V. Ciarlante
*Attorney, Agent, or Firm*—Flehr, Hohbach, Test, Albritton & Herbert

[57] ABSTRACT

A sector scanner having an oscillating transducer element includes a motor and rotating shaft, a crank attached to an end of the shaft, and a linkage connecting the crank and the oscillating transducer element whereby rotation of the shaft is translated to oscillation of the transducer element. Vibration from the oscillating transducer element is minimized by reducing the mass of the oscillating element and employing harmonic motion of the transducer element.

9 Claims, 14 Drawing Figures

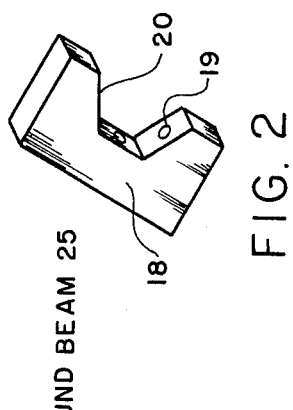
FIG. 2
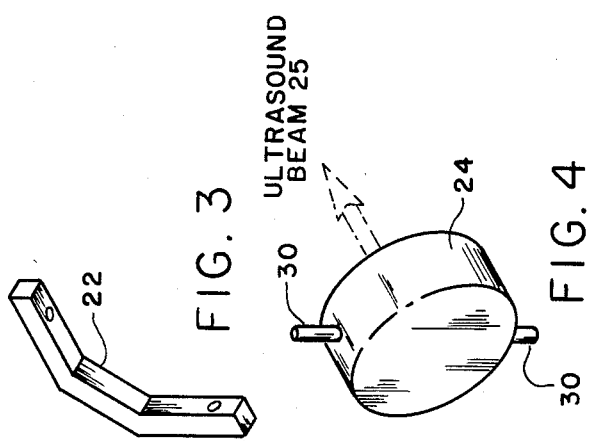
FIG. 3
FIG. 4
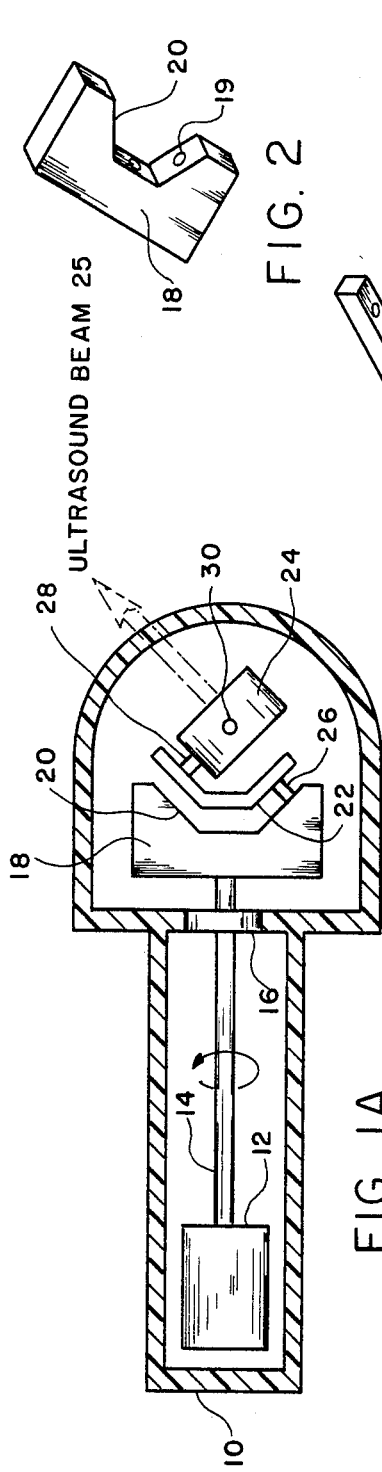
FIG. 1A
NOTE: P.N. 26 & PN 28 ARE ON OPPOSITE ENDS OF LINK 22
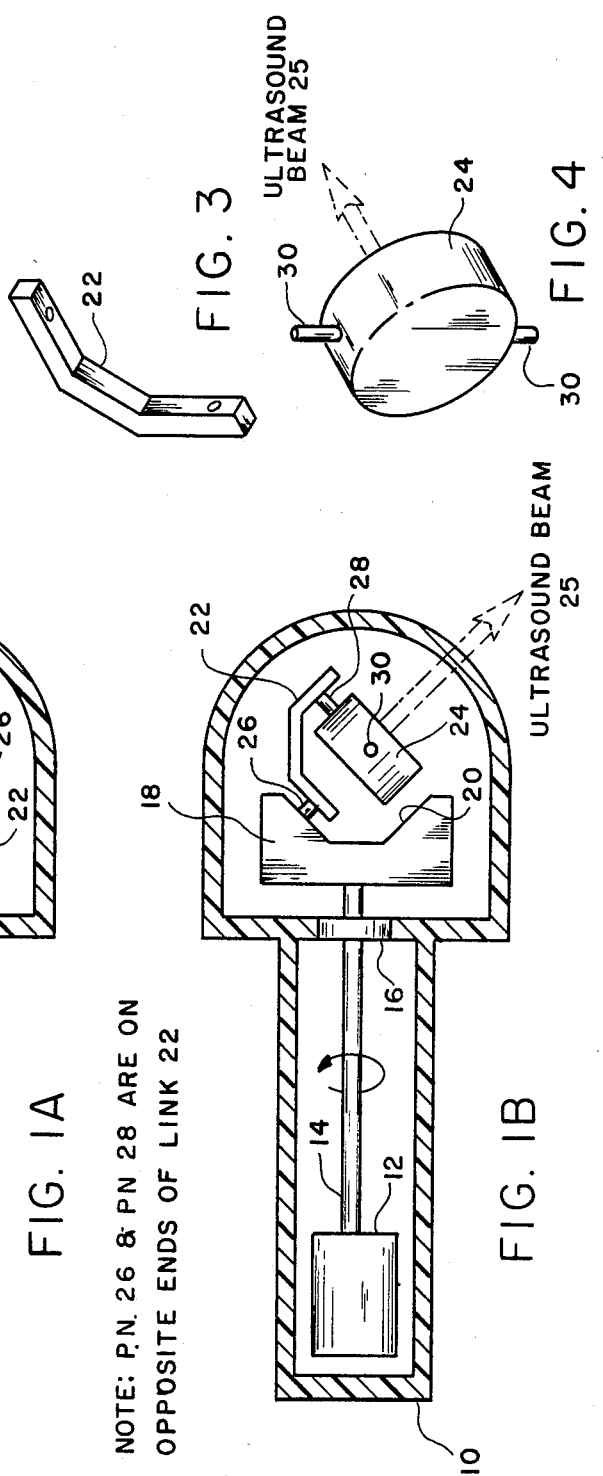
FIG. 1B

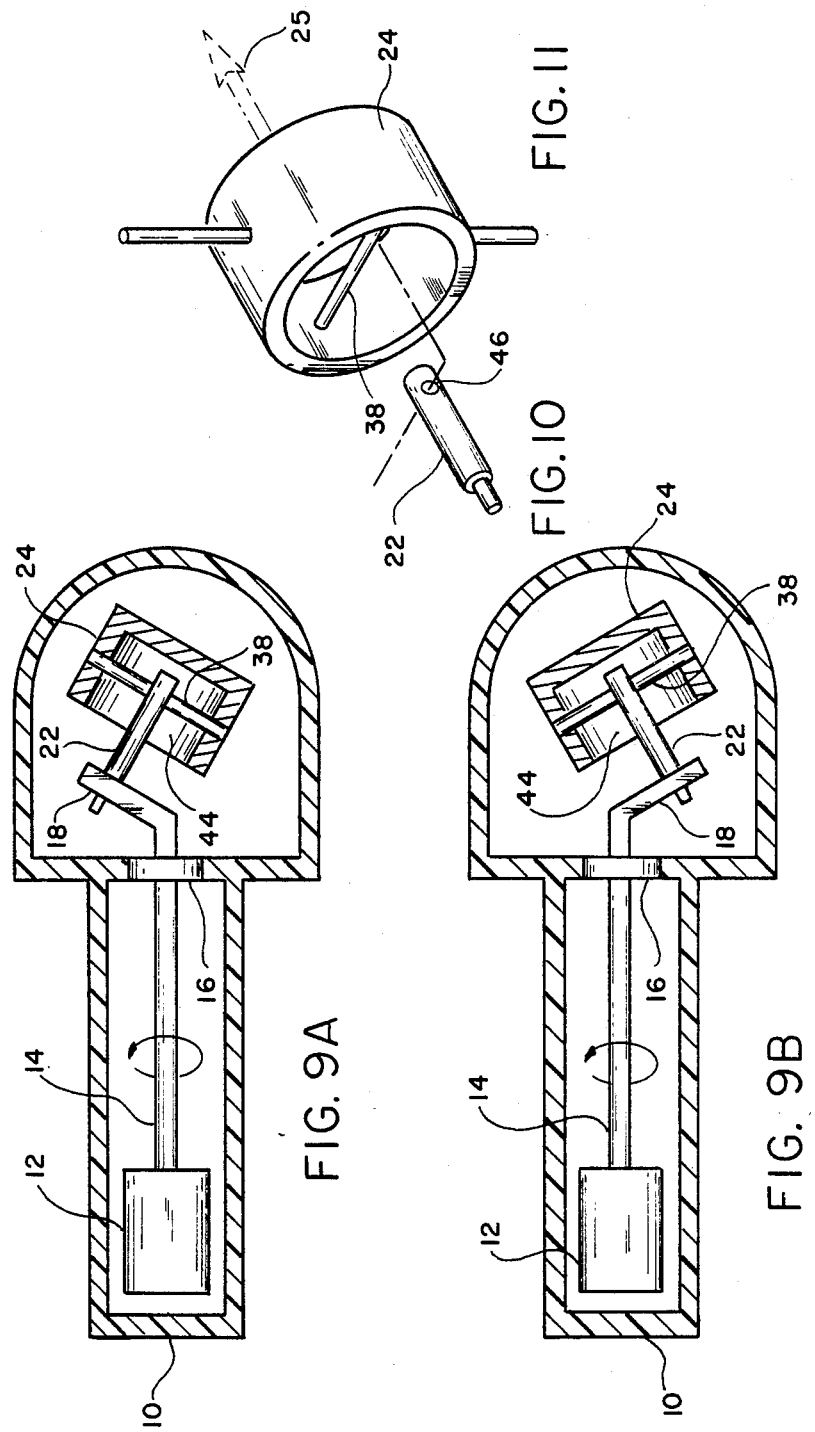

OSCILLATING SCANNER AND DRIVE MECHANISM THEREFOR

This invention relates generally to oscillating scanners such as used in ultrasonic diagnostic systems, and more particularly the invention relates to a drive mechanism for an oscillating scanner.

The oscillating ultrasonic transducer is used to obtain a wider field of view than is available with either a fixed wide aperture transducer or a linear phased array of transducer elements.

A number of mechanical schemes have been proposed for oscillating the transducer elements. U.S. Pat. No. 4,282,879 discloses use of a universal joint mechanism for converting a rotational drive to an oscillating scan. U.S. Pat. No. 4,277,979 utilizes a linkage attached to a rotating wheel to impart oscillatory motion. U.S. Pat. No. 4,298,009 discloses a stepper motor driven mechanism for oscillating and laterally translating a transducer element.

Major problems in driving an oscillating element stem from the large physical size of the drive mechanism and the excess in vibration of the driven element. By its nature, an oscillating mass will cause vibration. This is due to the inertia of the moving mass when changing direction through the oscillation cycle. Particularly for use in a handheld sector scanner, the scanner must be physically small since the physical size has a direct impact on the ergonomics and the aesthetics of the scanner.

Accordingly, an object of the present invention is an improved mechanism for driving an oscillated element.

Another object of the invention is an oscillated scanner having reduced vibration.

Yet another object of the invention is an oscillating drive mechanism which is physically small.

A further object of the invention is an oscillating scanner having reduced mass.

A feature of the invention is a mechanism for imparting harmonic motion to an oscillated mass.

Briefly, a drive mechanism in accordance with the invention includes a rotating shaft and crank, a connecting link, and an oscillating element. The shaft and oscillating element have perpendicular axes which intersect at a point. Two axes associated with the connecting link also intersect the point. The connecting link forms an angle with the axis of the rotating shaft which is one-half the angle of oscillation.

In accordance with another feature of the invention servo control of the mechanism is readily implemented since the harmonic displacement of the oscillating element is predictable as a function of time.

The invention and objects and features thereof will be more readily apparent from the following detailed description and appended claims when taken with the drawing, in which:

FIGS. 1A and 1B are side views of an oscillating scanner in accordance with one embodiment of the invention.

FIGS. 2–4 are perspective views of elements of the scanner of FIGS. 1A and 1B.

FIGS. 9A and 9B are side views of an oscillating scanner in accordance with yet another embodiment of the invention.

FIGS. 10 and 11 are perspective views of elements of the scanner of FIGS. 9A and 9B.

Figure 6:
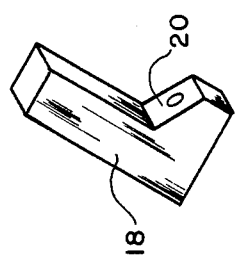
FIGS. 6–8 are perspective views of elements of the scanner of FIGS. 5A and 5B.

Like elements in these several views have the same reference numerals. Referring now to the drawing, FIGS. 1A and 1B are side views of an oscillating scanner in accordance with one embodiment of the invention, with the oscillating element at two extremes of oscillation. The scanner includes a housing 10 (shown in section to review the interior elements) in which are mounted a drive motor 12 having a shaft 14 which extends through a bushing 16. Mounted to the end of shaft 14 is a crank member 18 having inclined outer surfaces 20 which accommodate a linkage 22 and an oscillating transducer element 24. Linkage 22 is attached to one of the inclined surfaces 20 by a pivot pin 26 about which the linkage 22 is free to rotate. The opposite end of linkage 22 is attached to the oscillating transducer element 24 by a pivot pin 28. The oscillating element 24 is pivotally mounted in the housing 10 by means of pins 30 located on opposite sides of the elements 24.

FIGS. 2–4 are perspective views of elements of the scanner of FIGS. 1A and 1B. Crank member 18 has a hole 19 for accommodating the pivot pin 26 which attaches the linkage 22 shown in FIG. 3 to the crank member 18. The oscillating transducer 24 and pins 30 are shown in FIG. 4. The axes of shaft 14, pivot pins 26 and 28, and pins 30 have a common intersection point with the axes of shaft 14 and pins 30 forming a right angle, the axes of pin 26 and pin 30 forming a right angle, and the axis of pin 28 and pins 30 forming a right angle.

In operation, motor 12 rotates shaft 14 and crank member 18 as indicated in FIGS. 1A and 1B. As crank 18 rotates, the linkage 22 rotates on the pivot pin 26 and also extends outwardly from the crank member 18 thereby moving the oscillating element 24 about the axis of pivot pins 30. FIG. 1B illustrates the oscillating scanner with the crank member 18 rotated 180° from the position of FIG. 1A and with the linkage 22 fully extended and the ultrasonic beam 25 translated to the opposite extreme of oscillated movement. Thus, as crank 18 rotates one revolution, transducer element 24 has one oscillating cycle. Operation of the drive mechanism is somewhat similar to the space crank in converting rotating motion to oscillating motion.

The axis of pivot pin 26 forms an angle with respect to the axis of the shaft 14 which is one-half of the oscillation angle of the ultrasonic transmission axis 25. It will be noted that the linkage 22 is configured for movement within the surfaces 20 of the crank 18. In the embodiment of FIGS. 1A and 1B the center of mass of the oscillated element 24 coincides with the axis of oscillation (e.g. axis of pins 30) thus minimizing the inertia of the oscillating element. However, the linkage and crank extend outside of the dimension of the oscillated element 24 thus requiring a larger housing.

Figure 7:
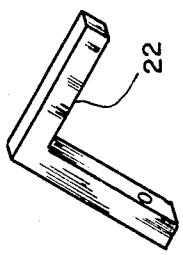
Figure 8:
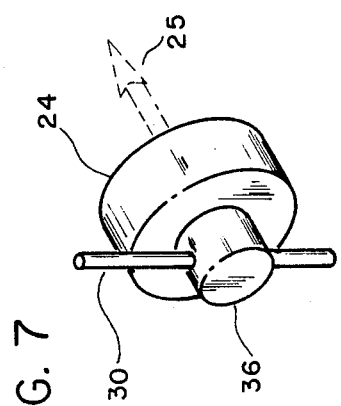
Figure 5A:
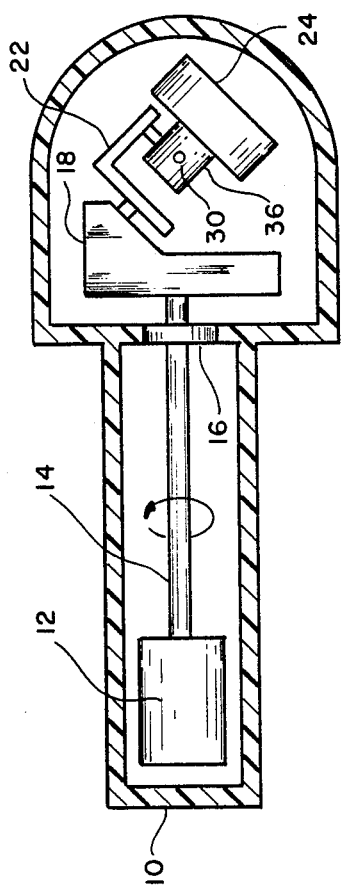
FIGS. 5A and 5B are side views of an oscillating scanner in accordance with another embodiment of the invention.
Figure 5B:
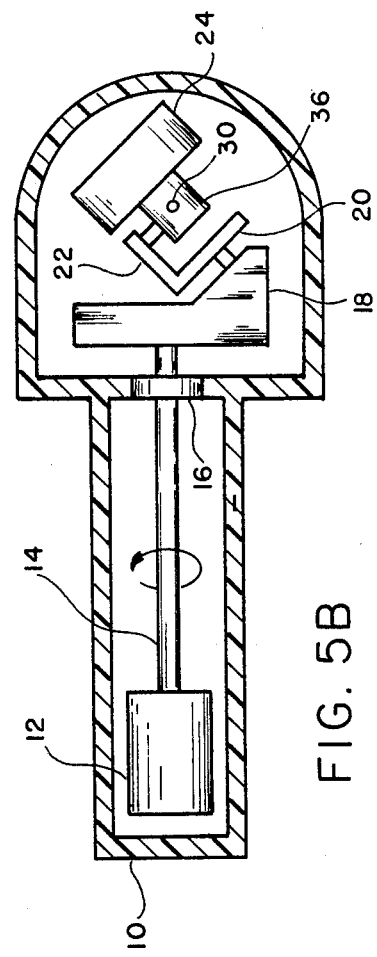

FIGS. 5A and 5B are side views of a sector scanner in accordance with another embodiment of the invention similar to the embodiment of FIGS. 1A and 1B but in which the crank and linkage have reduced size. Again, like elements have the same reference numerals. FIGS. 6–8 are perspective views of the crank 18, linkage 22, and transducer element 24 of this embodiment. In this embodiment the oscillating element 24 includes a portion 36 of reduced diameter and through which the supporting pivot pin 30 extends. Thus, by moving the axis of oscillation behind the oscillating element 24, the crank 18 and linkage 22 can be reduced in dimensions. However, since the center of mass of the element 24 does not coincide with the axis of oscillation 30, more vibration will be present in the operation of this embodiment of the invention than is present in operation of the embodiment of FIGS. 1A and 1B.

FIGS. 9A and 9B are side views of another embodiment of the invention in which the oscillating element 24 (shown in section) includes a concave portion 44 to reduce mass. Rod 38 extends across the concave portion 44 and has the same function as pin 28 in attaching the crank linkage 22 to the oscillating element 24. Provision is made for the linkage 22 to have relative rotation on the support rod 38 as the shaft 14 and crank 18 are rotated and the transducer element 24 is oscillated. FIGS. 10 and 11 are perspective views of the linkage 22 and transucer element 24. Hole 46 in linkage 22 slidably receives rod 38 of the element 24. This embodiment provides a reduced mass of the oscillated element and a reduction in the size of the linkage 22.

The drive mechanism in accordance with the invention has proved to be particularly useful in a handheld ultrasonic scanner where size constraints as well as minimum vibration are desired parameters. While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. A drive mechanism comprising
   a housing, a drive motor having a rotating shaft and shaft axis, a crank member attached to said shaft for rotation therewith,
   an oscillating element pivotally attached to said housing and having an axis of oscillation, and
   a linkage member attached to said crank member and to said oscillating element for oscillating said oscillating element about said axis of oscillation as said shaft and crank member are rotated, said linkage member being attached by a first pin to said crank means, said first pin having a first axis, and said linkage member is attached by a second pin to said oscillating element, said second pin having a second axis, whereby said shaft axis, said axis of oscillation, said first axis, and said second axis intersect at a point.

2. The drive mechanism as defined by claim 1 wherein said shaft axis and said oscillation axis forms a right angle, said first axis and said oscillation axis form a right angle, and said second axis and said oscillation axis form a right angle.

3. The drive mechanism as defined by claim 1 wherein said linkage member is attached to the periphery of said oscillating element.

4. The drive mechanism as defined by claim 1 wherein said oscillating element includes a projecting portion, said axis of oscillation passing through said projecting portion and said linkage member being attached to said projecting portion.

5. An ultrasonic sector scanner comprising
   a housing,
   a drive motor mounted inside of said housing and having a rotating shaft and shaft axis,
   a crank member attached to said shaft for rotation therewith,
   an oscillating transducer element pivotally attached to said housing and having an axis of oscillation, and
   a linkage member attached to said crank member and to said oscillating transducer element for oscillating said transducer element about said axis for oscillation as said shaft and crank member are rotated, said linkage member is attached by a first pin to said crank means, said firt pin having a first axis, and said linkage member is attached by a second pin to said oscillating transducer element, said second pin having a second axis, whereby said shaft axis, said axis of operation, said first axis, and said second axis intersecting at a point.

6. The drive mechanism as defined by claim 5 wherein said shaft axis and said oscillation axis form a right angle, said first axis and said oscillation axis form a right angle, and said second axis and said oscillation axis form a right angle.

7. The sector scanner as defined by claim 5 wherein said linkage member is attached to the periphery of said oscillating transducer element.

8. The ultrasonic scanner as defined by claim 5 wherein said oscillating transducer element includes a projecting portion, said axis of oscillation extending through said projecting portion and said linkage member being attached to said projecting portion.

9. An ultrasonic sector scanner comprising
   a housing,
   a drive motor mounted inside of said housing and having a rotating shaft and shaft axis,
   a crank member attached to said shaft for rotation therewith,
   an oscillating transducer element pivotally attached to said housing and having an axis of oscillation, said oscillating transducer element including a concave portion, said axis of oscillation extending through said concave portion, and further including a support member attached to said transducer element and positioned across said concave portion, said linkage member being rotatably attached to said crank member and slidably attached to said support member, and a linkage member attached to said crank member and to said oscillating transducer element for oscillating said transducer element about said axis of oscillation as said shaft and crank member are rotated.

* * * * *